United States Patent [19]

Trainin et al.

[11] Patent Number: 4,621,135

[45] Date of Patent: Nov. 4, 1986

[54] NOVEL THF COMPOSITIONS

[75] Inventors: Nathan Trainin; Yigal Burstein, both of Rehovot, Israel

[73] Assignee: Yeda Research & Development Company, Ltd., Rehovot, Israel

[21] Appl. No.: 741,753

[22] Filed: Jun. 6, 1985

Related U.S. Application Data

[63] Continuation-in-part of Ser. No. 559,393, Dec. 8, 1983, abandoned, which is a continuation-in-part of Ser. No. 535,539, Sep. 23, 1983, abandoned, which is a continuation of Ser. No. 475,175, Mar. 14, 1983, abandoned, which is a continuation-in-part of Ser. No. 394,571, Jul. 2, 1982, abandoned, which is a continuation of Ser. No. 300,330, Sep. 8, 1981, abandoned, which is a continuation-in-part of Ser. No. 227,299, Jan. 22, 1981, abandoned, which is a continuation-in-part of Ser. No. 153,644, May 27, 1980, abandoned.

[51] Int. Cl.$^4$ .................. A61K 37/00; C07C 103/52
[52] U.S. Cl. .................. 530/328; 530/329; 530/331; 530/301; 514/885
[58] Field of Search .............. 260/112.5 R, 112 R; 424/95; 514/2, 14, 16, 18, 21, 885; 530/301, 328, 329, 331

[56] References Cited

U.S. PATENT DOCUMENTS

| | | | |
|---|---|---|---|
| 3,873,509 | 3/1975 | Meguro | 260/112.5 R |
| 4,002,602 | 1/1977 | Goldstein | 260/112.5 R |
| 4,079,127 | 3/1978 | Goldstein et al. | 260/112.5 R |
| 4,133,804 | 1/1979 | Bach et al. | 260/112 R |
| 4,148,886 | 4/1979 | Bach et al. | 260/112.5 R |
| 4,250,084 | 2/1981 | Trainin | 260/112 R |
| 4,374,828 | 2/1983 | Folkers et al. | 260/112 R |
| 4,377,511 | 3/1983 | Lopukhin et al. | 260/112 R |
| 4,505,898 | 3/1985 | Marks et al. | 514/18 |

FOREIGN PATENT DOCUMENTS 1541275 2/1979 United Kingdom .

OTHER PUBLICATIONS

*J. of Exptl. Med.*, vol. 132, No. 5 (1970), pp. 885–897, Trainin et al.
*Cellular Immunology*, 19, 151–157 (1975), Kook et al.
Cancer III in Comprehensive Therapy, 4, 49–57 (1978), Goldstein et al.

*Primary Examiner*—John Kight
*Assistant Examiner*—Nathan M. Nutter
*Attorney, Agent, or Firm*—Ladas & Parry

[57] ABSTRACT

Novel peptide materials having thymic humoral activity are disclosed having the respective amino acid sequences of:
Leu-Glu-Asp-Gly-Pro-Lys-Phe-Leu;
His-Pro-Leu-Pro-Asp-Leu-Tyr; and
Phe-Val-Leu These novel peptides can be isolated from natural thymus glands or can be prepared synthetically.

4 Claims, No Drawings

NOVEL THF COMPOSITIONS

BACKGROUND AND DISCUSSION OF THE PRIOR ART

This is a continuation-in-part application of U.S. patent application. Ser. No. 559,393, filed on Dec. 8, 1983 and now abandoned, which was a continuation-in-part application of U.S. patent application Ser. No. 535,539, filed on Sept. 23, 1983, now abandoned, which was a continuation application of U.S. patent application Ser. No. 475,175, filed on Mar. 14, 1983, now abandoned, which was a continuation-in-part application of U.S. patent application Ser. No. 394,571, filed on July 2, 1982, now abandoned, which was a continuation application of U.S. patent application Ser. No. 300,330 filed on Sept. 8, 1981, now abandoned, which was a continuation-in-part application of U.S. patent application Ser. No. 227,299, filed on Jan. 22, 1981, now abandoned, which was a continuation-in-part application of U.S. patent application Serial No. 153,644, filed on May 27, 1980, now abandoned.

The present invention relates to compositions obtainable from thymus glands and to synthetic versions thereof.

There has been increasing interest over the last years or so in extracts obtained from animal, particularly calf thymus, glands and their immunological characteristics.

A report by Allan J. Goldstein and Jeffrey L. Rossio in Comprehensive Therapy, 4, 49–57 (1978) notes that in addition to the material with which it is concerned (designated "thymosin") three other thymic factors have been well investigated. These were thymopoietins, serum thymic factor (STF) and thymic humoral factor (THF).

Thymopoietins (formerly called "thymin"), their preparations and uses have been described by Gideon Goldstein in, for example, Nature 247, pages 11-14 (1974) and U.S. Pat. Nos. 4,055,633; 4,077,949; 4,120,951 and 4,124,700. The thymopoietins are obtained from homogenized calf thymus by a sequence of dialysis, molecular exclusion chromatography and fractionating chromatography. Two active products are obtained designated as Thymopoietins I and II. Both of these are polypeptides having 49 amino acid residues. They differ, however, in the nature of the residues in the 1 and 43 positions. U.S. Pat. No. 4,002,740 describes the synthesis of a tridecapeptide which is said to have many of the properties of Thymopoietin II. U.S. Pat. No. 4,369,137 describes certain intermediates useful in preparation of a thymopoietin pentapeptide. U.S. Pat. Nos. 4,190,646; 4,261,886 and 4,397,842 describe peptides having thymopoietin activity.

Serum thymic factor, its preparations and properties has been described by J. F. Bach et al in Nature 266, pages 55–57 (1977) and U.S. Pat. Nos. 4,098,777; 4,133,804; and 4,148,886. It is obtained from pig blood by a sequence of defibrination, dialysis, concentration on a suitable filter, fractionation through a molecular sieve, chromatography on an ion exchange resin, further fractionation by thin layer chromatography and electrophoresis. The product appears to be a polypeptide having 9 amino acid resides. Peptides having structure similar to serum thymic factor are described in U.S. Pat. No. 4,301,065.

Thymosins, in addition to the discussion in Comprehensive Therapy referred to above, have been describe in U.S. Pat. Nos. 4,010,148; 4,079,127; 4,082,737; 4,116,951; 4,128,637 and 4,148,788. U.S. Pat. No. 4,010,148, for example, describes the production of thymosin fractions from homogenized mammalian thymus. The process involved is a multi-stage purification technique, the product of each stage being referred to as a "fraction". Thus, the product obtained simply by centrifuging the homogenized thymus is "Fraction 1". The product obtained after the homogenization and centrifuging and subsequent heat, acetone and ammonium sulfate treatment and finally ultracentrifuging the precipitate obtained with ammonium sulfate, collecting the product at 4° C. and desalting on a Sephadex G-25 (fine) column is "Fraction 5". Further treatment culminating with electrophoresis and collection of the first protein peak produces "Fraction 8". Fraction 8 is a polypeptide containing 108 amino acid residues. U.S. Pat. No. 4,128,637 makes it clear that in fact a variety of polypeptides having molecular weights from 1,200 to 14,000 can be obtained by such techniques and are termed "thymosins". U.S. Pat. No. 4,082,737 describes the production of a solid, stable, endotoxin-free composition comprising the mixture of polypeptides constituting Thymosin Fraction 5.

The Goldstein Comprehensive Therapy article referred to above describes the properties of one particular polypeptide designated as Thymosin $\alpha_1$ obtained from Thymosin Fraction 5. It is stated to be a polypeptide of 28 amino acid residues and having a molecular weight 3,108 and an isoelectric point at pH 4.2. This is also described and claimed in U.S. Pat. No. 4,079,127. The radioimmunoassay of Thymosin $\alpha_1$ is described in U.S. Pat. Nos. 4,264,571 and 4,339,427. Thymosin $\alpha_1$ fragments are described in U.S. Pat. Nos. 4,442,031 and 4,470,926. Bis-thymosin $\alpha_1$ is described in U.S. Pat. No. 4,396,605. Two related polypeptides, designated as Thymosin $\beta_3$ and Thymosin $\beta_4$ have been obtained from Thymosin factor 5. The first material has 50 amino acid residues while the second material has 43 amino acid residues. This is described in U.S. Pat. No. 4,297,276. Fragments of Thymosin $\beta_3$ and $\beta_4$ are described in U.S. Pat. No. 4,395,404. Thymosin $\beta_8$ and $\beta_9$ are described in U.S. Pat. Nos. 4,388,234 and 4,389,343.

A further product which has been obtained from thymus glands is the ubiquitous immunopoietic polypeptide (UB IP) described in U.S. Pat. Nos. 4,002,602 and 4,167,557 and Proceedings of the National Academy of Sciences 72, pages 11–15 (1975). It has a molecular weight of about 8,500 and contains 74 amino acid residues. Related peptide material is disclosed in U.S. Pat. Nos. 4,215,111 and 4,190,647.

Other thymus extracts have been described in U.S. Pat. Nos. 3,438,859; 3,466,367; 3,657,417; 4,239,498; 4,377,511 and 4,394,374 which describe production of extracts but do not describe the production of any particular polypeptide. U.S. Pat. No. 4,374,828 describes thymic extracts having specific amino acid content but without any particular amino acid sequences. Human serum prealbumin possessing thymus hormone-like properties is described in U.S. Pat. No. 4,046,877. An immunostimulating preparation from bacterial RNA is described in U.S. Pat. No. 4,389,396. Peptides disclosed as being useful in the thymus function area are described in U.S. Pat. Nos. 4,250 086; 4,320,118, 4,361,673; 4,389,342; and 4,428,938.

All of these products have been reported to be of some use in meeting problems of immuno deficiency. It has, however, been reported in the Proceedings of the Society for Experimental Biology and Medicine 159, pages 195-200 (1978) that thymopoietin, UB IP and serum thymic factor are ineffective in inducing thymus-dependent immuno-competence that is meaningful in the intact animal.

None of this prior art discloses or suggests the specific peptide compositions of the present invention having thymic humoral activity.

Thymic Humoral Factor (THF) has been described, for example, in Journal of Experimental Medicine, 132, pages 885-897 (1970), Journal of Experimental Medicine, 138, pages 1521-1532 (1972), Cellular Immunology 19, pages 151-157 (1975) and U.S. Pat. No. 4,250,084 all of which indicated successful clinical results in humans. Further results of clinical studies were reported at a meeting of the New York Academy of Sciences on Feb. 26, 1979. This prior art thymic humoral factor is designated THF I.

In arriving at a clinically useful THF I in accordance with the previous procedures described in the above publications and in U.S. Pat. No. 4,250,084, each active fraction containing THF I prepared in the course of the purification process was tested in respect to seven (7) different bioassays and only fractions exhibiting a positive reaction to all seven tests were subjected to further purification and use. Experience has now shown that the activity of THF I fractions need only be assayed for activity in the cAMP, PHA, ConA and MLC bioassays to arrive at biologically active fractions which may be administered clinically.

It has hitherto been thought that the THF I preparation previously described in U.S. Pat. No. 4,250,084, for example, was a simple polypeptide since it migrated as a single ninhydrin-positive spot in both thin layer chromatography and paper electrophoresis at pH 3.5. It further migrated as a single band in isoelectric focusing on polyacrylamide gels with an isoelectric point of 5.6 to 5.9. Although none of the amino acids noted in the preparation is aromatic, the THF I preparation was found to absorb ultraviolet light at 280 nm which is typical of aromatic materials. This property was also found useful in the isolation of the desired THF I fractions. It was also thought that the THF I preparation, as described, for example, in the above U.S. Patent, was a substantially pure polypeptide of molecular weight of about 3200. It was not though that this previously known THF I preparation could be further separated into fractions, could have a molecular weight change to less than about 3200 by simple gel filtration means, or could have any new fractions of molecular weight less than about 3200 that would retain the same complete bioassay profile reported previously for THF I.

It was then surprisingly found that the thymic humoral factor (THF I) previously known is not in fact a single compound, that when subjected to specific gel filtration a separation of products occurred and that the desired biological activity appeared to be confined to particular fractions. Furthermore, it was found that the desirable biologically active fractions were those which showed substantially no ultraviolet absorption at 280 nm. Fractions eluted from the gel filtration means preceding and succeeding the active fractions contained products which did have significant ultraviolet absorption at 280 nm.

Prior application Ser. No. 153,644 disclosed the isolation of a biologically active material of the thymic humoral type (designated as THF II) characterized by an apparent molecular weight of less than about 1800, the substantial absence of ultraviolet absorption at 280 nm and biological activity in all the cAMP, PHA, ConA and MLC bioassays. This prior application also disclosed a process for obtaining THF II which comprises subjecting THF I to gel filtration, employing a gel filtration medium having an exclusion limit of about 1,800 Daltons, and collecting the fractions which lack substantial ultraviolet absorption at 280 nm and show activity in all of cAMP, MLC, PHA and ConA bioassays. One particular gel filtration medium which has been found to be effective for the desired fractionation to obtain THF II is Biogel P-2 resin which is of the polyacrylamide gel bead type and has an exclusion limit of 1,800 Daltons. This resin is available from Bio-Rad Laboratories of Richmond, Calif. 94804.

The cAMP bioassay employed to assay the fractions obtained is described, for example, in Kook and Trainin, J. Exp. Med. 139, page 193 (1974), Kook and Trainin, J. Immunol. 114, page 157 (1975) and Kook, Umiel and Albala, Ann. N.Y. Acad. Sci. 249, page 349 (1975).

The MLC bioassay employed to assay the fractions obtained is described, for example, in Umiel and Trainin, Eur. J. Immuno. 5, page 85, (1975) and Kook, Umiel and Albala, Ann. N.Y. Acad. Sci. 249, page 349 (1975).

The PHA and ConA bioassays employed to assay the fractions obtained are described, for example, in Rotter and Trainin, Cell. Immunol. 16, page 413 (1975).

Prior Application Ser. No. 227,299 disclosed the isolation of a biologically active material of the thymic humoral type (designated as THF III) characterized by an apparent molecular weight of less than about 1500 and biological activity in all the cAMP, PHA, ConA and MLC bioassays. This prior application also disclosed a process for obtaining THF III which comprises subjecting THF II to adsorption on a reversed phase high performance liquid chromatography column, eluting the retained material from the column and collecting the fractions which show activity in all of the cAMP, PHA, ConA and MLC bioassays.

Prior applications Ser. Nos. 300,330 and 394,571 disclosed the isolation of a biologically active material of the thymic humoral type (designated as THF-7) characterized by an apparent molecular weight of 1500 or less and biological activity in all the cAMP, PHA, ConA and MLC bioassays. These prior applications also disclosed a process for obtaining THF-7 which comprises subjecting THF III to adsorption on a reversed phase high performance liquid chromatography column preequilibrated with pyridine formate, eluting the retained material from the column with a mixture of pyridine formate and n-propanol and collecting the fractions which show activity in all of the cAMP, PHA, ConA and MLC bioassays.

Prior applications Ser. Nos. 475,175 and 535,539 disclosed the treatment of THF-7 to further purification by reversed phase high performance liquid chromatography to produce a biologically active material designated as THF-8 gamma fraction. Prior application Ser. No. 559,393 disclosed the further separation of THF-8 gamma fraction into several biologically active materials designated as gamma 2, gamma 4 and gamma 5. The amino acid sequences for THF gamma 2, THF gamma 4 and THF gamma 5 were set forth in this prior application. Further analytical work has indicated that the previously reported amino acid sequences for THF gamma 2 and THF gamma 4 were in error.

SUMMARY OF THE INVENTION

In accordance with the present invention, materials are provided having thymic humoral activity and being selected from the class consisting of peptides having the following amino acid sequences:

Leu-Glu-Asp-Gly-Pro-Lys-Phe-Leu;
His-Pro-Leu-Pro-Asp-Leu-Tyr; and
Phe-Val-Leu

These materials can be isolated from natural thymus glands or can be produced synthetically.

DESCRIPTION OF THE INVENTION

The THF I starter material for the production of the novel materials of this invention is prepared by the method generally described in U.S. Pat. No. 4,250,084 referred to above, the disclosure of which is herein incorporated by reference.

In order to prepare THF I, frozen thymus, conveniently calf thymus, is homogenized in a suitable liquid medium, such as buffer or saline, the cell debris removed and further undesired constituents removed by ultracentrifuging (for example, at 90,000 to 150,000 g. for 2 to 5 hours) and filtration through suitable membrane filters, for example, of pore size 0.8 to 2.0 μm so as to produce liquid free of microorganisms which produce endotoxins. The sterile liquid so-obtained is then subjected to exhaustive dialysis and the product obtained lyophilized and redissolved in a suitable liquid medium. The dialysis is typically carried out against larger volumes of water, saline or phosphate buffer saline (PBS) for from 24 to 60 hours in the cold. Any suitable dialysis membrane which will permit materials of molecular weight less than 10,000, for example, to pass through, may be employed. Suitable membranes include cellophane dialysis bags. The lyophilized dialyzate is redissolved in, for example, distilled water, ammonium bicarbonate, PBS or tris-buffer and diluted to a suitable polypeptide concentration of 1 to 15 mg./ml. of solvent. The resulting solution is then subjected to gel filtration.

The media used and the number of stages required for gel filtration in the preparation of THF I starting material for this invention depend to some extent on the nature of the preliminary treatment and in particular on the nature of the medium employed for the dialysis step. If this permits the passage of only relatively low molecular weight materials, it may be possible to keep the gel filtration stages to a minimum. It will, however, in any case be necessary to remove low molecular weight materials. This can be done by eluting and retaining the void volume of a column having an exclusion limit of a few hundred Daltons, for example Sephadex G-10 (Pharmacia), which has an exclusion limit of 700 Daltons.

Further fractionation to produce THF I starting material is effected by gel filtration using gel filtration materials having an exclusion limit of around 5,000 Daltons, for example, Sephadex G-25 (Pharmacia). Typically the column is eluted with $10^{-3}$M ammonium bicarbonate at pH 8.0. The active fraction is determined by the four bioassays referred to above. If desired, a yet further fractionation can be carried out, for example, on DEAE-Sephadex A-25 (Pharmacia) using 0.1 M Tris-HCl or 0.1 M $NH_4HCO_3$ at pH 8.0 and developing with a linear concentration gradient of NaCl. Salts may be removed by filtration with a material having a low molecular weight exclusion limit, such as Sephadex G-10, and recovering the void volume.

The THF I starting material thus prepared is then passed through a bed of gel filtration material having an exclusion limit of about 1800 Daltons in accordance with the disclosure of prior application Ser. No. 153,644. The retained material is then eluted with water and the eluted material collected in fractions. The ultraviolet absorption at 280 nm is monitored for each fraction and each fraction is assayed in the cAMP, PHA, ConA and MLC bioassays. The initial fractions obtained have substantial ultraviolet absorption at 280 nm but do not have biological activity in all of the above four bioassays. The next group of fractions obtained have substantial absence of ultraviolet absorption at 280 nm but have biological activity in all of the above four bioassays. The succeeding group of fractions have substantial ultraviolet absorption at 280 nm but do not have biological activity in all of the above four bioassays. The desired THF II material having biological activity in all of the above four bioassays is found in the fractions having a ratio of elution volume ($V_e$) to void volume ($V_o$) of the gel filtration medium of from about 1.1 to about 1.4. The void volume of the gel filtration medium is measured by well-known techniques. One procedure for measuring void volume employs Blue Dextran 2000. This is a high molecular weight dextran having a molecular weight of 2,000,000 containing a blue dye and is obtainable from Pharmacia Fine Chemicals Inc. A 0.1 percent (weight/volume basis) aqueous solution of Blue Dextran 2000 is added to the column of gel filtration medium in an amount of 1 percent by volume based on the total volume of the gel filtration medium. Water is then added to the column and eluted at a rate of 0.95 ml./min. Elution fractions of 5.75 ml. are collected. The absorption at 600 nm is monitored for each fraction. The total elution volume collected up to and including the fraction having peak absorption at 600 nm represents the void volume of the gel filtration medium.

The biologically active fractions of THF II prepared as above are then combined and passed through a reversed phase high performance liquid chromatography medium. The adsorbed contents are eluted with a suitable solution and the fractions retained having biological activity in all of the above four bioassays. This retained material is designated THF III.

Suitable chromatography media useful to produce THF III are the commercially available surface modified inorganic supports having octyl ($C_8$) or octadecyl ($C_{18}$) bonded phases. Other bonded phases of hydrophobic nature that are used for reversed phase liquid chromatography, such as biphenyl or hexyl ($C_6$) to octadecyl ($C_{18}$), may be used. Two useful materials are commercially available under the trade names Lichrosorb RP-18 and Nucleosil $C_{18}$. The Nucleosil $C_{18}$ material is available in 5 and 10 micron diameter particle sizes from Macherey-Nagel and Co., Duren, West Germany. Another useful material is a HPLC column obtained from Altex Scientific Inc. of Berkeley, Calif.

The THF II material can be applied to the above chromatography medium in any convenient concentration, but it is preferred to use a solution prepared by lyophilizing THF II solution containing about 3 mg. protein and then dissolving the lyophilized material in 1 ml. distilled water.

The aqueous solutions useful for eluting the adsorbed THF III material from the above chromatography medium include those of salts having sodium, potassium, ammonium or pyridinium cations and acetate, phosphate or formate anions, for example, ranging in pH from 3.5 to 7.5. The salt concentration is about 50 mM to 300 mM. These aqueous solutions are then mixed with suitable organic eluants, such as n-propanol, i-propanol, ethanol or acetonitrile, with linear or nonlinear gradients ranging from 0–20% to 0–60% of the organic solvent. A gradient of 0–50% n-propanol in sodium or ammonium acetate, 50 mM, pH 6.5 is preferred to obtain THF III.

The biologically active fractions of THF III prepared as above are then combined and passed through a reversed phase high performance liquid chromatography medium. The same chromatography media suitable for production of THF III are useful for separation and recovery of THF-7. The chromatography medium is preferably preequilibrated with pyridine formate, such as at a concentration of 0.3 mM and at pH 4.0. The adsorbed material on the column is preferably eluted with a mixture of pyridine formate and n-propanol. A gradient of 7.5–25% by volume n-propanol is most preferred. The eluted material having biological activity in all of the above four bioassays is designated THF-7.

The biologically active fractions of THF-7 prepared as above are then combined and passed through a reversed phase high performance liquid chromatography column. The same chromatography media suitable for production of THF-7 are useful for separation and recovery of THF-8. A preferred material is Nucleosil $C_{18}$ (5 microns). The chromatography medium is preferably preequilibrated with 0.1% by volume trifluoroacetic acid at pH 2.0. The adsorbed material on the column is preferably eluted with a mixture of trifluoroacetic acid and n-propanol. A gradient of 8–35% by volume n-propanol is most preferred. The eluted material having biological activity in the PHA, ConA and MLC bioassays is designated THF-8.

THF-8 is composed of several peptide materials. These peptide materials can be separated into their individual components by an isocratic separation. This is accomplished by passing the above-prepared THF-8 through a reversed phase high performance liquid chromatography medium of the same type used above for recovery of THF-8. In this case, it is preequilibrated with a mixture of 0.1 M sodium perchlorate, 0.1% orthophosphoric acid and 22% acetonitrile. The adsorbed material on the column is preferably eluted with a solvent of the same composition as the preequilibration mixture. The elution pattern is monitored by UV absorption at 210 nm. The fractions to be retained for further consideration are those indicated by peaks in the 210 nm absorption data. The retained material should also be tested for presence of peptides and only peptide-containing material is to be further processed. Each of the above collected fractions which are peptides are then separately desalted by passing them separately through a reversed phase high performance liquid chromatography medium of the same type used above preequilibrated with a suitable volatile buffer. A preferred buffer system is 2 mM ammonium formate at pH 7.8 or 0.1% trifluoroacetic acid in 5% acetonitrile. The desalted peptide is then eluted from the column with a suitable volatile buffer and solvent. Preferably this is ammonium formate or trifluoracetate using a linear gradient of 5–50% acetonitrile. The elution pattern is followed by monitoring the absorption at 210 nm. The fractions to be retained for further consideration are those indicated by peaks in the 210 nm absorption data. The resulting desalted peptide fractions are tested for biological activity in the PHA, ConA and MLC bioassays. The THF-8 fractions having activity in all of the above three bioassays are designated THF gamma 2, THF gamma 4, and THF gamma 5, respectively.

The production of the novel peptides of the present invention from thymus glands is described in more detail in the following example:

EXAMPLE 1

Biologically active fractions of THF I prepared in accordance with the example of U.S. Pat. No. 4,250,084 except that the initial thymus glands were frozen before THF I production began, were combined to provide a liquid mixture containing 1 mg. protein. This liquid mixture was then lyophilized. The lyophilized material was then dissolved in 5 ml. distilled water and applied onto a column of Bio Gel P-2, obtained from Bio-Rad Laboratories of Richmond, Calif. The column was 2.9 cm. in diameter and 130 cm. in depth. The void volume ($V_o$) of the column had previously been determined by using Blue Dextran 2000 to be 270 ml. The column contents were then eluted with double distilled, pyrogen free water at 0.95 ml./min. flow rate and fractions of 5.75 ml. were collected at 4° C. The ultraviolet absorption at 230 and 280 nm was monitored for each fraction. Each fraction was also tested for biological activity in the cAMP, PHA, ConA and MLC bioassays. Two distinct and well-separated peaks of absorption were observed. The first peak of absorption was obtained for fractions eluted with elution volumes ($V_e$) ranging from 250 ml. to 330 ml. ($V_e/V_o$ ratios of 0.93 to 1.22). The second peak of absorption was obtained for fractions eluted with elution volumes ranging from 490 ml. to 550 ml. ($V_e/V_o$ ratios of 1.82 to 2.04). Fractions having biological activity in all of the above four bioassays were obtained principally at elution volumes of 322 ml. to 345 ml. ($V_e/V_o$ ratios of 2.29 to 1.28). Substantially all of these fractions having the desired biological activity had no absorption at 180 nm. Since this active material had initially been retained by the Bio Gel P-2 having an exclusion limit of about 1800 Daltons, it thus had an apparent molecular weight of less than about 1800. The active material in these fractions was designated as THF II.

Fractions of THF II prepared as described above were combined to provide a liquid mixture containing 3 mg. protein. This liquid mixture was then lyophilized. The lyophilized material was then dissolved in 1 ml. of distilled water and applied onto a reversed phase high performance liquid chromatography (HPLC) ($C_{18}$) column obtained from Altex Scientific Inc. of Berkeley, California. The column was 4.6 mm. in diameter and 250 mm. long and was preequilibrated with 50 mM sodium acetate at pH 6.5. The column contents were eluted by passing 50 mM sodium acetate at pH 6.5 through the column at a flow rate of 48 ml./hr. for 1 hr. The flow rate was then maintained at the same rate for 45 min. while substituting some of the sodium acetate solution with n-propanol at a linear gradient from 0 to 50% by volume. Fractions of 2 ml. each were collected at ambient temperature (about 22° C.). The column eluates were monitored by ultraviolet absorption at 230 nm and by fluorescent detection of primary amino groups (following a post-column reaction of aliquots with fluorescamine at pH 9.5). Each fraction was also tested for biological activity in the in vitro cAMP, PHA, ConA and MLC bioassays.

Two distinct and well-separated areas of absorption were observed which reacted, in addition, with fluorescamine. The first peak of absorption was obtained using a single buffer and eluted with elution volumes of 5–25 ml. The fluorescamine positive material eluted in the same area with elution volumes ranging from 5–45 ml. The second peak of ultraviolet absorption, which was also fluorescamine positive, was eluted following operation of the linear gradient of propanol with elution volumes ranging from 4–10 ml. (0–9% propanol). Fractions having biological activity in all of the above bioassays were obtained only at elution volumes of 12 ml. to 16 ml. (10–16% propanol). Substantially all of these fractions having the desired biological activity had some absorption at 230 nm but were fluorescamine negative. The active material in these fractions was designated as THF III.

Fractions of THF III prepared as described above were combined and lyophilized. The lyophilized material was then dissolved in distilled water and applied onto a reversed phase high performance liquid chromatography column described above which had been preequilibrated with 0.3 M pyridine formate at pH 4.0. The column contents were eluted by passing 0.3 M pyridine formate at pH 4.0 through the column at a flow rate of 24 ml./hr. for 12 min. The flow rate was then maintained at the same rate for 12 min. while substituting some of the pyridine formate with n-propanol at a linear gradient from 0 to 7.5% by volume. The flow rate was then maintained at the same rate for 54 min. while substituting some of the pyridine formate solution with n-propanol at a linear gradient from 7.5 to 25% by volume. Fractions of 1 ml. each were collected at ambient temperature (about 22° C.). Each fraction eluted with n-propanol was then analyzed for total amino acid content after hydrolysis and was subjected to the above four biological assay procedures. The fractions containing the material eluted from the column employing 14–18% by volume n-propanol had the maximum total amino acid content and also had positive results in the above four biological assays. The active material in these fractions was designated as THF-7.

High speed gel filtration of THF-7 on a column of TSK-GEL SW 2000 (an adsorbent material marketed by Toyo Soda Mfg. Co. of Japan) suggested an apparent molecular weight of 1500 Daltons or less since 1500 Daltons is the smallest molecular size resolved by this column.

Fractions of THF-7 prepared as described above were combined and concentrated to dryness under reduced pressure. The dried material was then dissolved in water and applied onto a reversed phase high performance liquid chromatography column employing Nucleosil $C_{18}$ (5 microns). The column was 4.3 mm. in diameter and 250 mm. long and was preequilibrated with 0.1% by volume trifluoroacetic acid (TFA) at pH 2.0. The column contents were eluted by passing 0.1% TFA at pH 2.0 through the column at a flow rate of 24 ml./hr. for 12 min. The flow rate was then maintained at the same value for 12 min. while substituting some of the TFA with n-propanol at a linear gradient from 0 to 8% by volume. The flow rate was then maintained at the same value for 86 min. while substituting some of the TFA with n-propanol at a linear gradient from 8 to 35% by volume. Fractions of 1 ml. each were collected at ambient temperature (about 22° C.). Each fraction eluted with n-propanol was then analyzed for total amino acid content after hydrolysis and was subjected to MLC, PHA and ConA in vitro biological assays. The fractions containing the material eluted from the column employing 16–22% by volume n-propanol had the maximum total amino acid content and also had positive results in the above three biological assays. The active material in these fractions was designated as THF-8.

Fractions of THF-8 prepared as described above were loaded onto a reversed phase high performance liquid chromatography column (4.3×200 mm.), such as Nucleosil $C_{18}$ (5 microns), which had been preequilibrated with a solution of 0.1 M sodium perchlorate, 0.1% orthophosphoric acid and 22% acetonitrile. The column contents were eluted with a solution of the above composition at a flow rate of 1.5 ml./min. Fractions of 1 ml. each were collected at ambient temperature (about 25° C.). The elution pattern was monitored by UV absorption at 210 nm. Fractions having increased absorption peaks were retained. Six major fractions were thus isolated. They were designated as THF-8 alpha, beta, gamma, delta, epsilon and theta fractions. Portions of all of the fractions other than alpha were completely digested by pronase and were at least partially digested by proteinase K. This indicated that the alpha fraction is not a peptide and the other fractions are all peptides.

The THF-8 beta, gamma, delta, epsilon and theta fractions were then each separately dried under reduced pressure, dissolved in water and desalted by applying them to separate reversed phase high performance liquid chromatography columns of the above composition which had been preequilibrated with 2 mM ammonium formate at pH 7.8 in 5% by volume acetonitrile. The desalted material was eluted from each column with 2 mM ammonium formate using a linear gradient of 5–50% acetonitrile at a flow rate of 1.5 ml./min. The elution pattern was followed by monitoring the absorption at 210 nm. Fractions of 1 ml. each were collected. Fractions having increased absorption peaks were retained. The beta fraction yielded two separate desalted peptide fractions while the other fractions yielded one desalted peptide fraction each. The resulting six desalted peptide fractions were designated as THF-8 beta-1, beta-2, gamma, delta, epsilon and theta. Each of these desalted peptide fractions were separately dried under reduced pressure and dissolved in water. Aliquot portions of each were then subjected to amino acid analysis after acid hydrolysis and to in vitro MLC (thymus), MLC (spleen), PHA and ConA bioassays. The THF-8 gamma fraction was the most active in all of the above four bioassays.

The biological activity of the above THF-8 gamma fraction was about one thousand times greater than that of THF-I. This is shown by the fact that the above bioassays could be conducted for THF-8 gamma fraction using nanogram levels while comparable bioassays for THF-I were in the microgram levels.

Clinical utility for THF-8 gamma fraction has also been demonstrated. It was used to restore immunologic T-cell function in a human patient suffering from a defective thymic epithelial anlage, causing dysmaturity of the T-cell lineage.

The above-prepared THF-8 gamma material was eluted from the chromatography column prior to desalting at a retention time of about 20 min. The above procedure for preparing the gamma fraction of THF-8 starting from calf thymus was repeated several times, and the gamma fractions from each preparation eluted at a retention time of about 20 min. were separately collected and retained. These collected fractions were then separately dried under reduced pressure, dissolved in water and desalted by the above-described procedure employing a reversed-phase high performance liquid chromatography system. The elution pattern was followed by monitoring the absorption at 210 nm. Fractions having increased absorption peaks were retained.

Three separate peptides of THF-8 gamma fraction were thus prepared. These peptides were analyzed for their amino acid content and for their amino acid sequences. They were also subjected to MLC, PHA and ConA bioassays. These peptides were designated THF gamma 2, THF gamma 4 and THF gamma 5. The results are shown below.

THF gamma 2 = Leu-Glu-Asp-Gly-Pro-Lys-Phe-Leu

THF gamma 4 = His-Pro-Leu-Pro-Asp-Leu-Tyr

THF gamma 5 = Phe-Val-Leu

Asp = Aspartic acid
Glu = Glutamic acid
Gly = Glycine
His = Histidine
Leu = Leucine
Lys = Lysine
Phe = Phenylalanine
Pro = Proline
Tyr = Tyrosine
Val = Valine All of these novel peptides had biological activity in each of the MLC, PHA and ConA bioassays.

The synthetic production of peptides THF gamma 2, THF gamma 4 and THF gamma 5 from amino acid raw materials is described in the following examples.

EXAMPLE 2

Using the amino acid sequence information for THF gamma 2, THF gamma 4 and THF gamma 5 obtained from Example 1 above, synthetic forms of these peptides were prepared using a modified Merrifield technique generally described in J. Am. Chem. Soc. 85, pp. 2149-2154(1963). In each case, the carboxy terminal residue of the desired peptide, protected at the amino group with t-butyloxycarbonyl (Boc), was coupled to a chloromethylated polystyrene divinylbenzene (1%) co-polymer, 200-400 mesh, (chlorine content 0.7 meq./g), in boiling ethanol under reflux for 72 hr. The resin polymer was used in a quantity of 2-10 g and the initial amount of t-Boc-amino acid was used in an amount of 0.7 mmol/g of resin. The yield of coupling was 0.15-0.3 mmole Boc-amino acid/g polymer. The N-protected amino acid resin was washed sequentially with 100 ml ethanol, 100 ml 50 volume percent ethanol in dichloromethane and 100 ml dichloromethane. The washed N-protected amino acid resin was transferred to a 250 ml. Teflon bottle and placed in an agitator/shaker or in a peptide synthesizer, such as Model 001 Peptider (Peninsula Laboratories, Inc., Belmont, Calif. The subsequent synthesis steps were carried out in the same bottle. All synthesis steps were carried out at room temperature. For each subsequent amino acid moiety to be added to the peptide the following cycle of operations was carried out starting with the N-protected amino acid resin: (1) wash three times with 40-80 ml. dichloromethane for each wash; (2) remove the previous Boc protective group with two separate treatments of 40-80 ml. 50 volume percent trifluoroacetic acid in dichloromethane for 15 min. each; (3) wash three times with 40-80 ml. dichloromethane for each wash; (4) wash three times with 40-80 ml. 50 volume percent ethanol in dichloromethane for each wash; (5) wash three times with 40-80 ml. dichloromethane for each wash; (6) neutralize for 5 min. each with two separate 40-80 ml portions of 5 volume percent diisopropylethylamine in dichloromethane; (7) wash six times with 40-80 ml. dichloromethane for each wash; (8) add 3 equivalents of the next desired Boc-protected amino acid in 4-8 ml dimethylformamide and 3 equivalents of N,N'-dicyclohexylcarbodiimide in 30-72 ml dichloromethane and mix for 2 hr.; (9) wash three times with 40-80 ml 50 volume percent ethanol in dichloromethane for each wash; (10) wash three times with 40-80 ml dichloromethane for each wash; (11) repeat step (8) above overnight; and (12) wash three times with 40-80 ml 50 volume percent ethanol in dichloromethane for each wash.

After the above twelve-step cycle was repeated a sufficient number of times to synthesize the desired peptide, the protected peptide resin was then cycled through the above steps (1) to (5) inclusive and dried. It was then treated with liquid HF (4 ml/g), anisole (1 ml/g) and thioanisole (1.5 ml/g) for 30 minutes at 0° C. to remove the protecting groups and to separate the peptide from the resin. The HF was then evaporated. The crude peptide was precipitated by adding 100-200 ml diethyl ether at 0° C. The precipitate was separated from the ether solution by filtration and was dried. The dry peptide precipitate was then extracted with 100-300 ml 50 volume percent aqueous acetic acid and any insolubles removed by filtration. The solvent was then evaporated, and the resulting residue was dissolved in water and passed through a Sephadex G-15 or Biogel P-2 gel filtration column. The adsorbed peptide was eluted with water and the eluate was monitored by ultraviolet absorption at 254 nm. The fractions having peptide peak at this absorption wavelength were collected. These peptide fractions were then loaded onto a Lichrosorb RP-18 reversed phase high performance liquid chromatography column (10×250 mm) which had been preequilibrated with 0.1 M sodium perchlorate and 0.1% by volume phosphoric acid in 23% by volume aqueous acetonitrile. The material was then eluted from the column with the same solvent under isocratic conditions at a flow rate of 5 ml/min. The elution pattern was followed by monitoring the absorption at 210 nm. Fractions of 7.5 ml each were collected. Fractions having increased absorption peaks were retained. The fractions containing the desired peptide were concentrated under reduced pressure and loaded onto a reversed phase HPLC column (such as described above) which had been preequilibrated with 0.1 volume percent trifluoroacetic acid in 5 volume percent aqueous acetonitrile. The peptide was then eluted with 0.1 volume percent aqueous trifluoroacetic acid using a linear gradient of 5-50% acetonitrile at a flow rate of 5 ml/min. The elution pattern was followed by monitoring the absorption at 210 nm. Fractions of 7.5 ml each were collected. Fractions having increased absorption were retained since they contained the desired peptide. The purified peptide was then analyzed for amino acid content and amino acid sequence to verify its structure.

The above procedure was followed to produce synthetic THF gamma 2 in an overall yield of 11 mole percent based on the initial amount of the first amino acid moiety coupled to the resin. During the synthesis procedure, the trifunctional amino acids glutamic acid and aspartic acid were further protected with benzyl esters, and the lysine was further protected with o-chlorobenzyloxy-carbonyl. This resulting synthetic peptide had the following amino acid sequence:

Leu-Glu-Asp-Gly-Pro-Lys-Phe-Leu

This material was biologically active in the range of 0.5–50 ng/ml in the in vitro bioassays and in the range of 1–80 ng/kg body weight in the in vivo bioassays. The in vivo bioassays established the use of synthetic THF gamma 2 in restoring impaired immunological functions of neonatally thymectomized mice.

EXAMPLE 3

The above procedure was followed to produce synthetic THF gamma 4 in an overall yield of 24 mole percent having the following amino acid sequence:

His-Pro-Leu-Pro-Asp-Leu-Tyr

During the synthesis procedure, the aspartic acid was further protected with benzyl ester, and the histidine was further protected with N-tosyl-imidazole. This material was biologically active in the range of 5–80 ng/ml in the in vitro bioassays.

EXAMPLE 4

The above procedure was followed to produce synthetic THF gamma 5 in an overall yield of 35 mole percent having the following amino acid sequence:

Phe-Val-Leu

This material was biologically active in the range of 50–250 ng/ml in the in vitro bioassays and in the range of 20–1000 ng/kg body weight in the in vivo bioassays. The in vivo bioassays established the use of synthetic THF gamma 5 in restoring impaired immunological functions of neonatally thymectomized mice.

What is claimed is:

1. A material having thymic humoral activity and being selected from the class consisting of peptides having the following amino acid sequences:
    Leu-Glu-Asp-Gly-Pro-Lys-Phe-Leu;
    His-Pro-Leu-Pro-Asp-Leu-Tyr; and Phe-Val-Leu.
2. A peptide material having thymic humoral activity and having the following amino acid sequence:
    Leu-Glu-Asp-Gly-Pro-Lys-Phe-Leu.
3. A peptide material having thymic humoral activity and having the following amino acid sequence:
    His-Pro-Leu-Pro-Asp-Leu-Tyr.
4. A peptide material having thymic humoral activity and having the following amino acid sequence:
    Phe-Val-Leu.

* * * * *